United States Patent
Eilbert

(10) Patent No.: US 7,324,625 B2
(45) Date of Patent: Jan. 29, 2008

(54) CONTRABAND DETECTION SYSTEMS USING A LARGE-ANGLE CONE BEAM CT SYSTEM

(75) Inventor: Richard F. Eilbert, Lincoln, MA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 0 days.

(21) Appl. No.: 11/139,193

(22) Filed: May 27, 2005

(65) Prior Publication Data

US 2005/0276376 A1 Dec. 15, 2005

Related U.S. Application Data

(60) Provisional application No. 60/575,104, filed on May 27, 2004.

(51) Int. Cl.
*G01N 23/10* (2006.01)
*G01N 23/087* (2006.01)

(52) U.S. Cl. .......................... 378/57; 378/98.9

(58) Field of Classification Search .............. 378/4, 378/5, 15, 16, 19, 57, 98.9, 98.11, 98.8; 250/370.09
See application file for complete search history.

(56) References Cited

U.S. PATENT DOCUMENTS

| | | | | |
|---|---|---|---|---|
| 5,182,764 A * | 1/1993 | Peschmann et al. | .......... | 378/57 |
| 5,291,402 A * | 3/1994 | Pfoh | .......... | 378/13 |
| 5,367,552 A | 11/1994 | Peschmann | | |
| 5,661,774 A * | 8/1997 | Gordon et al. | .......... | 378/101 |
| 5,838,758 A * | 11/1998 | Krug et al. | .......... | 378/53 |
| 5,909,477 A | 6/1999 | Crawford et al. | | |
| 5,943,388 A | 8/1999 | Tümer | | |
| 5,982,845 A * | 11/1999 | Sidoti et al. | .......... | 378/4 |
| 6,078,642 A | 6/2000 | Simanovsky et al. | | |
| 6,301,324 B1 * | 10/2001 | Pearson et al. | .......... | 378/15 |
| 6,459,755 B1 * | 10/2002 | Li | .......... | 378/4 |
| 6,504,894 B2 * | 1/2003 | Pan et al. | .......... | 378/8 |
| 6,574,299 B1 * | 6/2003 | Katsevich | .......... | 378/15 |
| 6,816,571 B2 * | 11/2004 | Bijjani et al. | .......... | 378/57 |
| 6,922,462 B2 * | 7/2005 | Acharya et al. | .......... | 378/98.11 |
| 6,990,170 B2 * | 1/2006 | Sugihara et al. | .......... | 378/15 |

(Continued)

OTHER PUBLICATIONS

Eilbert, Richard F., et al., "Aspects of Image Recognition in Vivid Technologies Dual Energy X-Ray System," *Proceedings of SPIE*, vol. 1824, Nov. 1992, pp. 127-143.

(Continued)

*Primary Examiner*—Allen C. Ho
(74) *Attorney, Agent, or Firm*—Wolf, Greenfield & Sacks, P.C.

(57) ABSTRACT

A contraband detection system using a cone beam computed tomography scanner. The cone beam scanner allows for rapid acquisition of data for computing three dimensional density maps of objects within items under inspection. Where greater resolution is desired, the image information obtained with the cone beam computed tomography scanner may be combined with higher resolution images formed with a single view scanner. A multi-energy single view scanner may be used to additionally provide information on the effective atomic number of objects contained within items under inspection. Additionally, information obtained with the cone beam computed tomography scanner may be used to increase the accuracy of the computation of the effective atomic number of objects within the item under inspection.

6 Claims, 6 Drawing Sheets

U.S. PATENT DOCUMENTS

| | | | |
|---|---|---|---|
| 7,016,458 B2 * | 3/2006 | Francke | 378/19 |
| 7,103,137 B2 * | 9/2006 | Seppi et al. | 378/9 |
| 7,116,751 B2 * | 10/2006 | Ellenbogen et al. | 378/57 |
| 2002/0071524 A1 | 6/2002 | Renkart et al. | |
| 2003/0128804 A1 | 7/2003 | Poteet et al. | |
| 2004/0017888 A1 | 1/2004 | Seppi et al. | |
| 2004/0109532 A1 * | 6/2004 | Ford et al. | 378/57 |
| 2005/0031069 A1 * | 2/2005 | Kaucic et al. | 378/19 |

OTHER PUBLICATIONS

Eilbert, Richard F., "Development and Evaluation of Simulants for X-Ray Based Explosive Detection Systems," *Proceedings of the Second Explosives Detection Technology Symposium & Aviation Security Technology Conference*, Nov. 1996, pp. 49-54.

Grangeat, Pierre, "Mathematical Framework of Cone Beam 3D Reconstruction Via the First Derivative of the Radon Transform," *Mathematical Methods in Tomography (Lecture Notes in Mathematics 1497)*, ed. G.T. Herman, et al. (Berlin: Springer) (1991), pp. 66-97.

Horn, Berthold K.P., "Density Reconstruction Using Arbitrary Ray-Sampling Schemes," *Proceedings of the IEEE*, vol. 66, No. 5, May 1978, pp. 551-562.

Kachelrieβ, Marc, et al., "Advanced single-slice rebinning for tilted spiral cone-beam CT," *Med. Phys.* 28 (6), Jun. 2001, pp. 1033-1041.

Katsevich, Alexander, "Theoretically exact FBP-type inversion algorithm for spiral CT," *SIAM J Appl Math*, vol. 62, (2002), pp. 2012-2026.

Lauritsch, Günther, et al., "Exact consideration of data redundancies for spiral cone-beam CT," *SPIE International Symposium Medical Imaging, Image Processing*, San Diego, California, Feb. 2004, pp. 1-12.

Silver, Michael D., "High-helical-pitch, cone-beam computed tomography," *Phys. Med. Biol.* 43 (1998), pp. 847-855.

Zou, Yu, et al., "Exact Image Reconstruction on P1-lines in Helical Cone-beam CT," *Phys. Med. Biol.* 49 (2004), pp. 941-959.

Search Report Dated Dec. 19, 2005.

Written Opinion of the International Preliminary Examining Authority in PCT/US2005/018846, dated Jul. 4, 2006.

* cited by examiner

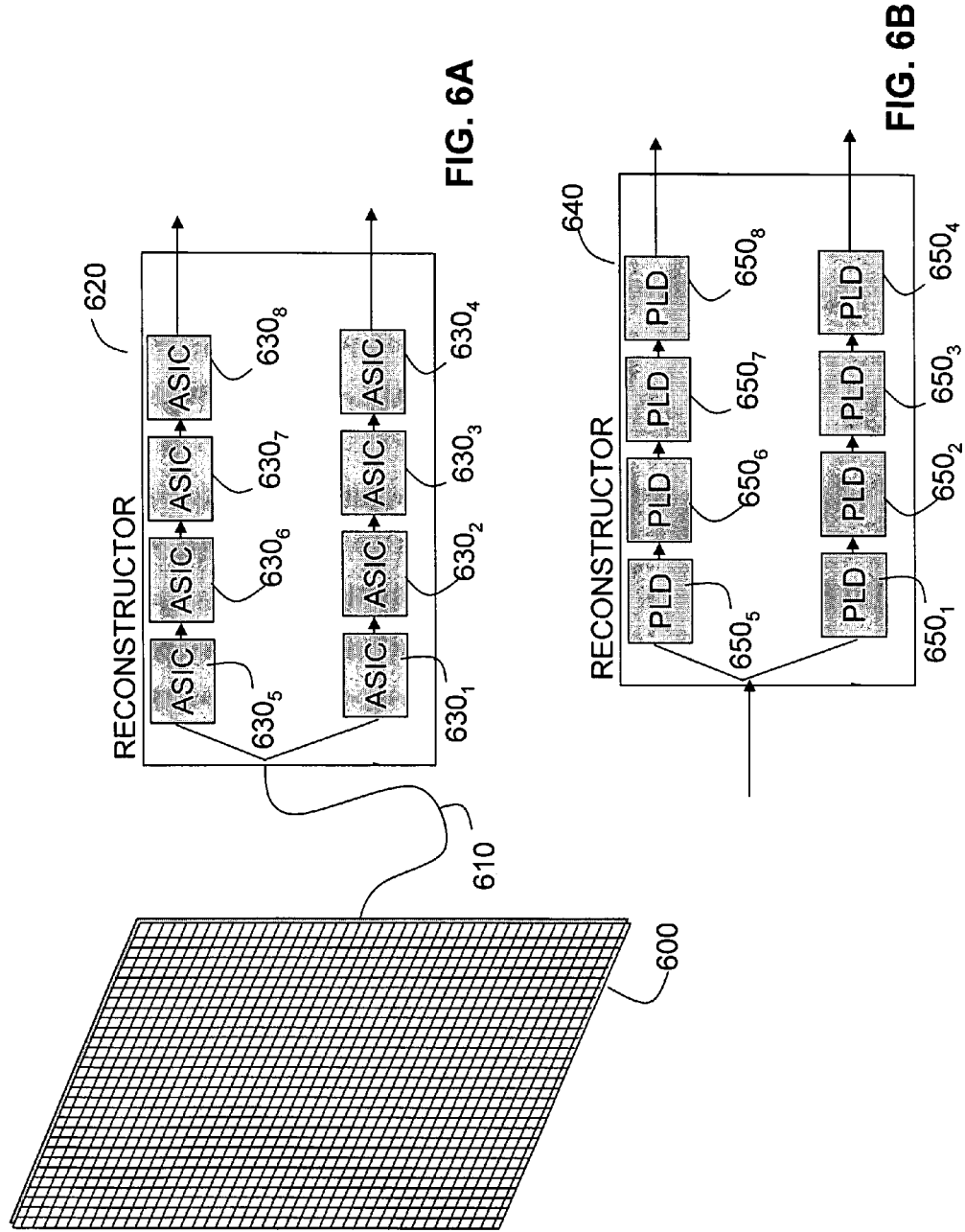

CONTRABAND DETECTION SYSTEMS USING A LARGE-ANGLE CONE BEAM CT SYSTEM

RELATED APPLICATIONS

This application claims priority under 35 U.S.C. § 119(e) to U.S. Provisional Application Ser. No. 60/575,104, entitled "X-RAY INSPECTION USING A LARGE-ANGLE CONE BEAM CT SYSTEM," filed on May 27, 2004, which is herein incorporated by reference in its entirety.

BACKGROUND OF INVENTION

1. Field of Invention

The invention relates generally to contraband detection systems and more specifically to x-ray inspection systems employed for contraband detection.

2. Discussion of Related Art

Contraband detection systems are used to rapidly detect contraband concealed in items under inspection. Such systems are used for security applications to detect weapons or explosives hidden in items such as luggage or cargo containers. Many types of contraband detection systems are in use.

Many contraband detection systems detect contraband by forming images using x-rays or, more generally, penetrating radiation. These systems contain a radiation source that emits radiation toward an item under inspection. A detector can array is used to measure the magnitude of the radiation after it has passed through the item under inspection. The measured radiation is used to compute properties of the item under inspection.

Different types of system may have different arrangements of the source and detectors or may process the detected radiation differently or compute different properties. For example, single view systems project radiation through the item under inspection in a single direction. An image formed with a single view system represents a projection of objects within the item into a single plane. In contrast, a computed tomography system (often called a "CT system") uses a rotating source and rotating detector array to measure radiation passing through the item under inspection from multiple angles. These measurements are used to compute the density of small regions arrayed in a slice through the item under inspection.

Many systems are scanning systems, meaning that the item under inspection moves relative to the radiation source/detector combination. Often, the item under inspection moves on a belt past the source and detectors. Radiation measurements are taken at successive intervals as the item under inspection passes the detector arrays. Each set of measurements is used to create a portion of the image of the item under inspection. For example, in a single view system, the detector array is often a linear array that is transverse to the direction of motion of the belt. Each measurement taken with the detector array provides information for one line in an image. The successive measurements can be combined to form a projection of the entire item under inspection. In a CT system, multiple slices through an item under inspection can be combined to form a three dimensional model of the item.

CT systems used for contraband detection are called small-angle cone beam CT or alternatively fan beam CT, although this latter term is somewhat confusing as the term "fan" more typically refers to the beam angle along the detector array. Small-angle cone beam CT have divergences up to around +/−2 degrees, meaning that the beam may have an angle of about +/−2 degrees in a direction transverse to the axis of rotation of the source.

Small-angle cone beam CT systems typically contain detector arrays that are as wide as the beam at the point where the beam intersects the detector array. Wider arrays can be formed by including multiple rows of detectors in the array. Multiple rows of detectors allow data from which multiple slices can be constructed to be collected at one time. For example, previous CT's, such as the Examiner inspection system sold by the assignee of the present application, have a sampling width of about 13 cm, made up of 24 rows of detectors about 5 mm wide.

The data from the multiple rows of detectors is usually processed using algorithms that assume the radiation from the source to each of the rows of detectors in the array travels in parallel planes. If the beam diverges, this assumption is not exactly true, but so long as the divergence is relatively small, the deviation does not significantly impact the resultant image. Other processing techniques interpolate to measurements that would have been obtained had the rays traveled in parallel planes. So long as the divergence is small, such interpolations are sufficiently accurate. Large-angle cone beam CT systems, sometimes called simply cone beam CT systems, have been used in medical applications. Data processing techniques that do not rely on the assumption that radiation reaches all rows of detectors in parallel planes have been developed for these applications. For many years, the Feldkamp (FDK) method, as described in Feldkamp, L. A., L. C. Davis and J. W. Kress, "Practical cone-beam algorithm", J. Opt Soc. of Am. 1(6), pp. 612-619 (1984) was considered the best choice for CBCT reconstruction. Advances made by Grangeat as described in Grangeat, P., "Mathematical framework of cone-beam 3D reconstruction via the first derivative of the Radon transform," Mathematical Methods in Tomography, G. T. Herman, A. K. Louis and F. Natterer, eds., Lecture Notes in Mathematics, 1497, pp. 66-97, Springer-Verlag, Berlin (1991) established a new methodology toward exact reconstruction, linking the projection data to a derivative of 3-D Radon transform. Kasevitch succeeded in reducing this formalism to filtered back-projection technique that is both fast and accurate, as described in Kasevitch, A., "An improved exact filtered back-projection algorithm for spiral computed tomography," Adv. Appl. Math. 32(4), pp. 681-697 (2004) and Kasevitch, A., "Theoretically exact FBP-type inversion algorithm for spiral CT," SIAM Jour. Appl. Math., 62, pp. 2012-2026 (2002).

SUMMARY OF INVENTION

In one aspect, the invention relates to a contraband detection system that has a gantry rotating about an axis and having an opening therethrough. The system has an inspection area within the opening. A radiation source is mounted on the gantry, emitting a beam of radiation toward the inspection area. The beam has a divergence along the axis. A detector array is positioned on the gantry and has a width along the axis sufficient to intersect the beam across a divergence of at least +/−3 degrees.

In another aspect, the invention relates to a method of analyzing an item for the presence of contraband. the method involves forming a projection image of the item with a first resolution using a multi-energy scanner. A computed tomography image of the item with a second resolution, less than the first resolution, is formed using a cone beam computed tomography scanner. Based at least on the projection image and the computed tomography image, an image representative of an object within the item, including an indication of an effective atomic number of the object is formed.

In another aspect, the invention relates to a method of operating a contraband detection system to inspect an item. As part of the method, the item is passed through the contraband detection system. While the item is passing through the contraband detection system, a radiation source and a detector array are moved around the item and about an axis of rotation. Radiation from the source is detected with the detector array, wherein the detector array has an extent of at least 5 degrees along the axis of rotation relative to an apex at the source.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6 is a sketch of a portion of an inspection system.

DETAILED DESCRIPTION

Figure 1:
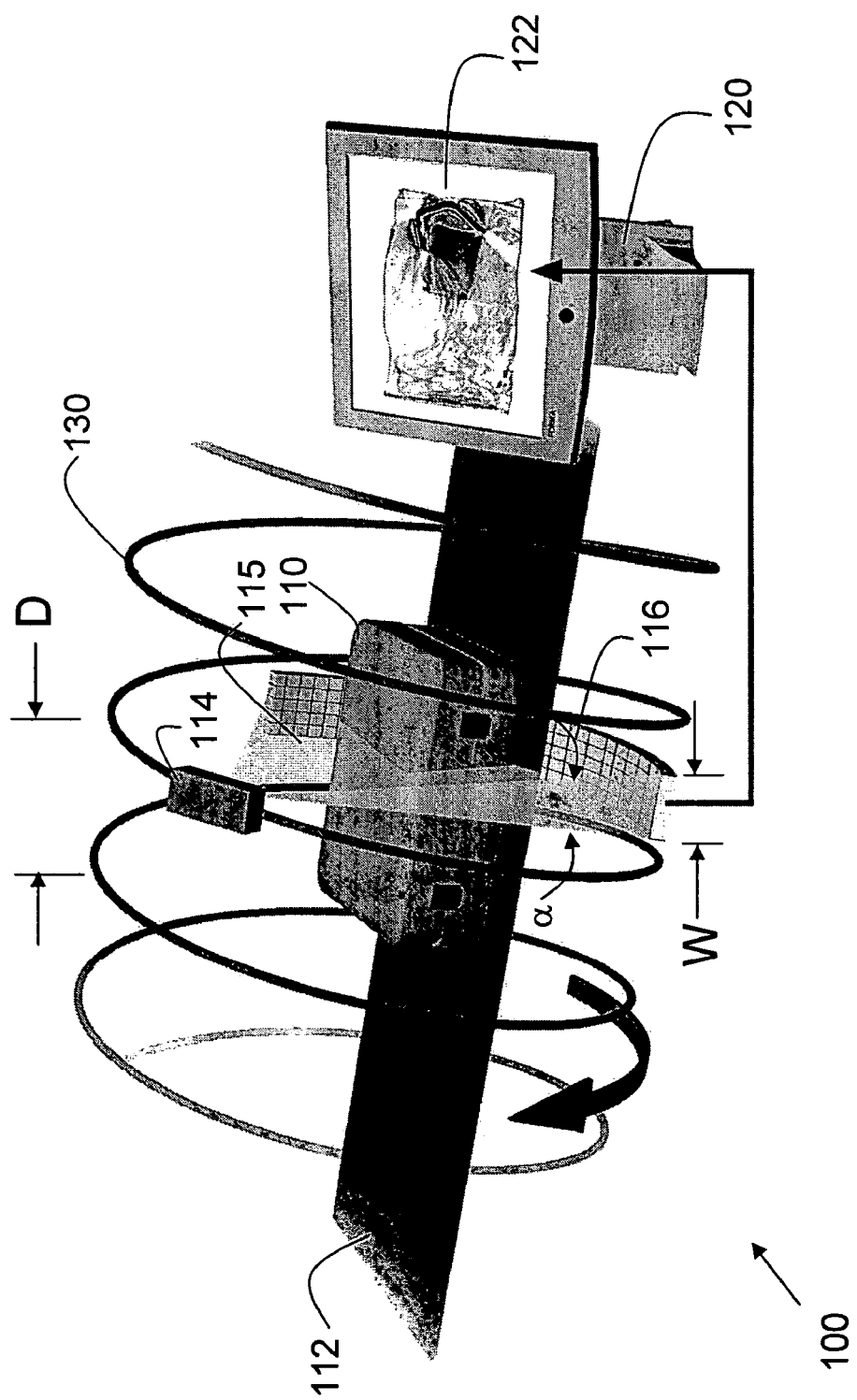
FIG. 1 is a sketch of a baggage inspection system using a large-angle cone beam.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

An improved contraband detection system is provided with a large-angle cone beam CT system. The system provides high throughput and can accurately detect contraband. Greatly increased throughput is accomplished via large-angle cone-beam computed tomography (cone beam CT). In some embodiments, the system can provide high-resolution reconstructions at rates exceeding 100 per sec.

In some embodiments, the system includes a dual energy single view (SV) scanner, which can serve multiple purposes. First, a single view system can economically provide high resolution bag imaging that significantly exceeds current regulatory requirements. Second, the SV scanner can provide atomic number ($Z_{eff}$) information for objects of interest within items under inspection. Atomic number information, or other information obtained from a single view system can be fused with density or other information derived from CT images. Combining information such as effective atomic number and density information increases accuracy of threat detection.

In some embodiments, the system has capabilities including: 1500 bags per hour throughput, 105 cm by 82 cm tunnel aperture and a false alarm rate below 10%. The system can incorporate cone beam CT in baggage scanning and detection based on combined $Z_{eff}$ and density over a full 3-D reconstruction.

FIG. 1 illustrates a contraband detection system employing a cone beam CT imaging sub-system 100, which is illustrated in FIG. 1 inspecting a suitcase 110. Cone beam CT imaging sub-system 100 may be a portion of a contraband detection system installed at a security check point at an airport. Such a system may be used to inspect carry-on luggage being brought onto an airplane. However, use of a cone beam CT imaging sub-system is not limited to airport security checkpoints. Such a sub-system could be used for other types of inspection functions at airports, such as inspecting checked luggage for contraband. Moreover, such a sub-system may be used in other settings. For example, it may be used to inspect cargo containers for contraband or may be used to inspect parcels or other items in any setting where it is desired to determine whether the item contains a contraband object.

CT imaging sub-system 100 includes source 114 that delivers beam 115 of penetrating radiation. Beam 115 has a divergence α of greater than +/−2 degrees (i.e. a total beam angle of approximately four degrees). In some embodiments, the divergence α will be approximately +/−3 degrees (i.e. a total beam angle of approximately six degrees) and in other embodiments +/−5 degrees (i.e. a total beam angle of approximately ten degrees).

Any suitable type of penetrating radiation may be used to construct an inspection system. Penetrating radiation is sometimes referred to colloquially as "x-rays," but the term "x-rays" is sometimes used to signify penetrating radiation in a specific frequency band. Penetrating radiation outside that frequency band, such as radiation described as gamma rays, may also be used.

Source 114 may be a radiation source, whether now known or hereafter developed, as is used in a conventional CT system for contraband detection. Such sources produce beams with divergences greater than is desired in a conventional system. To reduce emission of radiation from the inspection system, the source is traditionally fitted with a collimator that restricts the radiation emanating from the source to a plane or to a narrow-angle cone beam that has a relatively small divergence. To create a beam suitable for a large-angle cone beam CT system, the same source may be used without a collimator or with a widened collimator that passes a beam with the desired divergence. The x-ray photons needed for reconstruction accuracy are typically available by merely widening the collimator, without need for increasing the source strength.

Beam 115 intersects detector array 116. Detector array 116 includes multiple detectors that are sensitive to radiation generated by source 114. In contrast to a traditional CT imaging sub-system, detector array 116 is wider, and may have a sampling width in excess of 20 cm.

Detector array 116 is illustrated having a width, W, that is wide enough to intersect the bean 115 across a divergence α. In some embodiments, detector array 116 has a width, W, sized to intersect a beam across a divergence of about +/−5 degrees, resulting in a detector width of around 30 cm. Though, in other embodiments, the width may be around 25 cm.

Detector array 116 may contain multiple rows of detectors. Each row adds to the width of the detector array. In some embodiments, detector array 116 will contain at least 32 rows of detectors.

In operation, source 114 and detector array 116 rotate around an inspection area. Outputs of the detectors are sampled to obtain measurements of the detector outputs at successive instances. The measurements represent radiation passing through different regions of the item under inspection. To facilitate rotation, the source and detector array may be mounted on a gantry (not shown), as in a conventional CT inspection system. In some embodiments, the gantry may rotate at a fixed speed in the 30 to 120 rpm range.

In FIG. 1, suitcase 110 is shown in the inspection area as an example of an item under inspection. Beam 115 between source 114 and detector array 116 passes through an inspection area and, at any time, intersects suitcase 110 through a region that may be represented by multiple planes passing between the source and one of the rows of detectors in array 116.

The item under inspection may move relative to the source/detector such that the entire item is scanned. FIG. 1 shows a helix 130, representing the relative path of the source relative to the item under inspection. Similar results may be obtained regardless of whether the source moves relative to the item under inspection or the item under inspection moves. In the described embodiment, the item under inspection is placed on a conveyor 112 that moves the item under inspection past the source. In this way, the outputs of the detectors at successive times may be used to form images of different locations of the item under inspection, allowing an image of the entire item under inspection to be formed.

The speed at which conveyor 112 moves the item under inspection is not a limitation on the invention. However, by moving each item more quickly through the inspection system, the overall throughput of the system is increased. Because detector array 116 has more rows of detectors than a more conventional system, a greater portion of the bag will be sampled during each revolution of the x-ray source. Between successive samples, conveyor 112 may move the item under inspection a distance equal to the portion of the bag for which data is collected during one sample. By providing a wider detector area over which samples are taken, the speed of conveyor 112 may be increased, and may, for example, be roughly 2.4 times faster than in a conventional contraband detection system.

Each of the detectors in array 116 outputs a value representing the magnitude of radiation reaching the detector. As in a traditional CT system, the relative magnitudes of the radiation measurements indicate attenuation of radiation along a path through the item under inspection. These measurements made by each of the detectors can be processed to create an image of an item under inspection.

The outputs of the detectors are passed to a data processing system 120. Data processing system 120 may contain a display 122 that presents an image of an item under inspection. Display 122 may be a computer display, such as a CRT or a TFT. However, the display need not be expressly connected to a computer. The display could be printed output or presented on any other media.

The displayed image of the item contains a correspondence between regions of the item under inspection and regions of the display. Each region of the display is given visually perceptible characteristics based on physical characteristics of the corresponding region of the item under inspection as determined by measurements taken by the inspection system. In this way, the image presented on display 122 may have visually identifiable regions that "show" objects inside the item under inspection that have identifiable characteristics.

A display 122 may present information about an item under inspection to an operator of a contraband detection system. The human operator may study the image to detect objects within the item that could represent contraband. However, it is not necessary that the output of data processing system 120 be presented to a human operator. The "image" may be in electronic form, with an array of values, each value corresponding to a region of the item under inspection and having a value representing a characteristic of that region. The image in this electronic form may be provided to one or more computers where the image is processed. For example, a computer may apply automated threat detection algorithms to an electronic image instead of or in addition to human processing of the image to detect possible contraband objects within the item under inspection.

Data processing system 120 may include local data processing circuitry to reconstruct images of items inspected by the CT scanner. A "reconstructor" for a CT scanner provides a means to transform measurements at the outputs of the detectors representing attenuation data into data representative of density in multiple volume elements ("voxels").

In one embodiment, the reconstructor includes special data processing hardware located with the scanner. However, the attenuation may be transmitted over a network or other communication link to data processing hardware. This latter arrangement allows for very high speed data processing hardware to be shared by multiple inspection stations. The hardware could be implemented as a general purpose computer programmed to perform image reconstruction. Alternatively, special purpose hardware might be used to perform the entire reconstruction or might be used as a hardware accelerator in conjunction with one or more general purpose computers.

In one embodiment, the reconstructor is implemented using FPGAs or other programmable logic devices (PLD). A portion of the reconstruction computation may be implemented in each FPGA. Hardware to perform a full reconstruction may be made by pipelining multiple FPGAs by forming multiple parallel chains of pipelined FPGAs. To accommodate the large amounts of data that must be processed to reconstruct a wide angle cone beam CT image, high speed FPGAs may be employed. Alternatively, mask programmed logic devices may be used. As yet a further alternative, ASICs could be used to deliver even greater computational speeds to process the data at the rate it is being generated.

For example, FIG. 6A illustrates a detector array 600 coupled to a reconstructor 620 through optical coupling 610. In the illustrated embodiment, reconstructor 620 is implemented from ASICs configured in a plurality of pipelined chains. In FIG. 6A, ASICs $630_1 \ldots 630_4$ are shown forming one chain and ASICs $630_5 \ldots 630_8$ form another chain. FIG. 6B illustrates an alternative embodiment of a reconstructor. Reconstructor 650 is implemented with PLD's such as FPGA's, also implemented in a plurality of pipelined chains. In FIG. 6B, PLDs $650_1 \ldots 650_4$ are shown forming one chain and PLDs $650_5 \ldots 650_8$ form another chain.

In some embodiments data will be transferred from the detectors at a rate of about 150 MByte/sec. The reconstructor may operate at this rate or faster, though the reconstructor may operate at a slower rate by buffering data. Processing at 150 MByte/sec allows for reconstruction of 2 mm voxels and an x-ray source rotating at 1.5 rev/sec at 1500 mm diameter (7500 mm circumference). Detector dimension of about 4 mm yield 2 mm resolution.

As one example, a system to achieve the required resolution may have a detector array spanning 120 deg of arc (60 deg beam angle) and covers 2500 mm and so requires 625 detectors of 4 mm width in each row. To provide 4 mm between samples with the source moving at a rate of 7500 mm/sec, a sample rate of 1875 samples/sec may be used. With data transferred in the form of 16 bit numbers, the overall data rate can be computed as: 625 detectors×64 rows×1875 samples/sec×16 bit=1200 Mbit=150 MByte/sec.

This data rate corresponds to 240 degrees of rotation and amounts to 150 MByte. Even if 1 to 2 rotations must be buffered, the fast-access storage requirement of 256 or 512 MByte of memory would be adequate, though more fast access memory may be used.

Various algorithms exist to construct an image of an item using ct data. Variations of those algorithms also exist. One possible variation relates to the amount of data used to reconstruct a slice of an item under inspection. Data gathered during a partial revolution of the source around the inspection area may be sufficient to accurately construct a representation of a slice. Accuracy improvement occurs by using data from one and a half turns (3-PI) which adds redundancy. The redundancy adds computation time and increases the memory requirements for data buffers. Accordingly, a specific system design may tradeoff accuracy for processing power.

The connections within the inspection system may be any connection suitable for passing the required amount of information. For example, communication bandwidth from a printed circuit board on which the reconstructor is implemented to an image acquisition computer may be equal to or greater than the amount of data that needs to be transmitted. Transferring 150 reconstructions/sec of estimated size 512 by 512 pixels calls for a rate of 80 MByte/sec. Optical couplings may be used to transfer data at this rate. Alternatively, a traditional high-speed slip ring, which can support 225 MByte/sec data rates, may be used to transfer data from the rotating gantry holding the source and detector arrays. In some embodiments, error correcting communication protocols are used to transmit the information.

Though a reconstructor located locally with the inspection system is used in some embodiments, processors implemented the reconstructors need not be physically located at the inspection location. The detector array may be connected to any one or more processors that may be located remotely from the inspection location.

Regardless of the specific implementation of the reconstructor, it may construct an image using data processing techniques appropriate for large-angle cone beam CT systems. An algorithm that provides a theoretically exact reconstruction may be used. Algorithms, such as those described in Radon, J., "On the determination of functions from their integral values along certain manifolds", (English translation), IEEE Trans. Med. Imaging 5, pp. 170-176 (1986); translated from "Uber die bestimmung von funktionen durch ihre integralwerte langs gewisser mannigfaltigkeiten," Berichte Sachsische Akademie der Wissenschaft, Leipzig, Mathematisch-Physikalische Klasse, 69, pp. 262-277 (1917); Kachelriess, M., T. Fuchs, S. Schaller, W. A. Kalender, "Advanced single-slice rebinning for tilted spiral cone-beam CT", Med Phys. 28(6), pp. 1033-1041 (2001); Feldkamp, L. A., L. C. Davis and J. W. Kress, "Practical cone-beam algorithm", J. Opt Soc. of Am. 1(6), pp. 612-619 (1984) (sometimes referred to as FDK) (all of the foregoing of which are hereby incorporated by reference in their entireties). Alternatively, techniques such as those known as advanced single slice rebinning (ASSR) and limited region of interest (LROI). In one embodiment, an algorithm as defined in U.S. Pat. No. 6,574,299 to Katsevich (which is hereby incorporated by reference) may be used. Such a processing approach provides a reconstruction that is efficient and exact.

Figure 2:
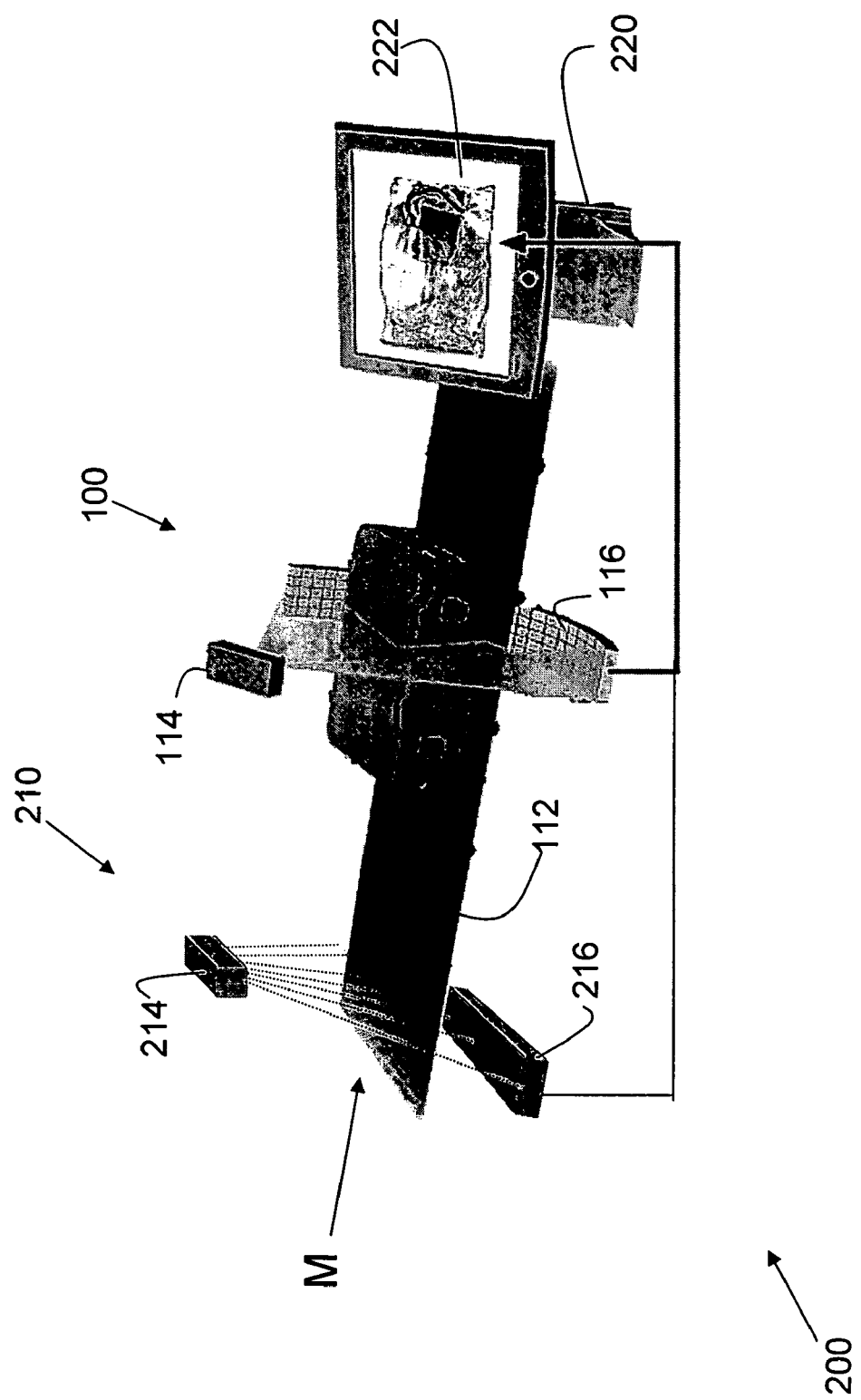
FIG. 2 is a sketch of an alternative embodiment of a baggage system.

FIG. 2 shows an alternative embodiment of a contraband detection system 200. In the embodiment of FIG. 2, cone beam CT imaging sub-system 100 is used in connection with a second imaging sub-system 210. Data from the two imaging subsystems is provided to a data processing system 220. Data processing system 220, as with data processing system 120, may contain components to create an image from the large-angle cone beam CT data and may additionally contain components that process the data generated by the second imaging sub-system. The resulting image may be presented on display 222.

In the example of FIG. 2, the second imaging sub-system is a single view imaging sub-system 210. Single view imaging sub-system 210 includes a source 214 and a detector array 216. Source 214 may emit a beam of penetrating radiation that has relatively little divergence. Detector array 216 may contain multiple detectors. In this embodiment, the detectors are arrayed in a single row.

In the illustrated embodiment, single view imaging sub-system 210 is a scanning type system. Samples of the outputs of the detectors are taken at successive intervals as an item under inspection moves past detector array 216 on conveyor 112. These samples are provided to data processing system 220 that can create a projection image of the item under inspection.

In one embodiment, the detectors in detector array 216 are smaller than the detectors in detector array 116 used in cone beam CT imaging sub-system 100. In this way, the image formed using the single view imaging sub-system 210 may have higher resolution than the CT image formed by cone beam CT imaging sub-system 100. Nonetheless, the total amount of data that is generated by the single view imaging sub-system 210 may be less than generated by cone beam CT imaging sub-system 100 because of the number of different directions from which data must be collected to construct each of the many slices needed to represent an item with data gathered by cone beam CT imaging sub-system 100.

Additionally, single view imaging sub-system 210 may employ imaging techniques to derive further information about the item under inspection that may be fused with information generated by cone beam CT imaging sub-system 100. In one embodiment, single view imaging sub-system 210 uses dual-energy imaging techniques to acquire information about the effective atomic number of objects within the item under inspection.

The addition of a dual-energy single view imaging sub-system 210 adds another dimension to the detection ability of the system. True dual energy systems employ two x-ray beams operated at different energies, either by constructing source 214 as a switching source or using two separate sources, each providing a beam of radiation at a different energy. However, dual energy measurements can be obtained by using one x-ray source providing an x-ray spectrum including energy at least two energy levels incident on a detector array that can separately measure incident radiation at more than one energy level. A detector array sensitive to multiple energies may be made in one of multiple ways. Such a detector array may be constructed from two detector arrays, with detectors in each array responsive to different parts of the x-ray spectrum. A detector can be made to respond to different parts of the x-ray spectrum by varying the type of scintillator material, its thickness and/or its pre-filtration.

Figure 3:
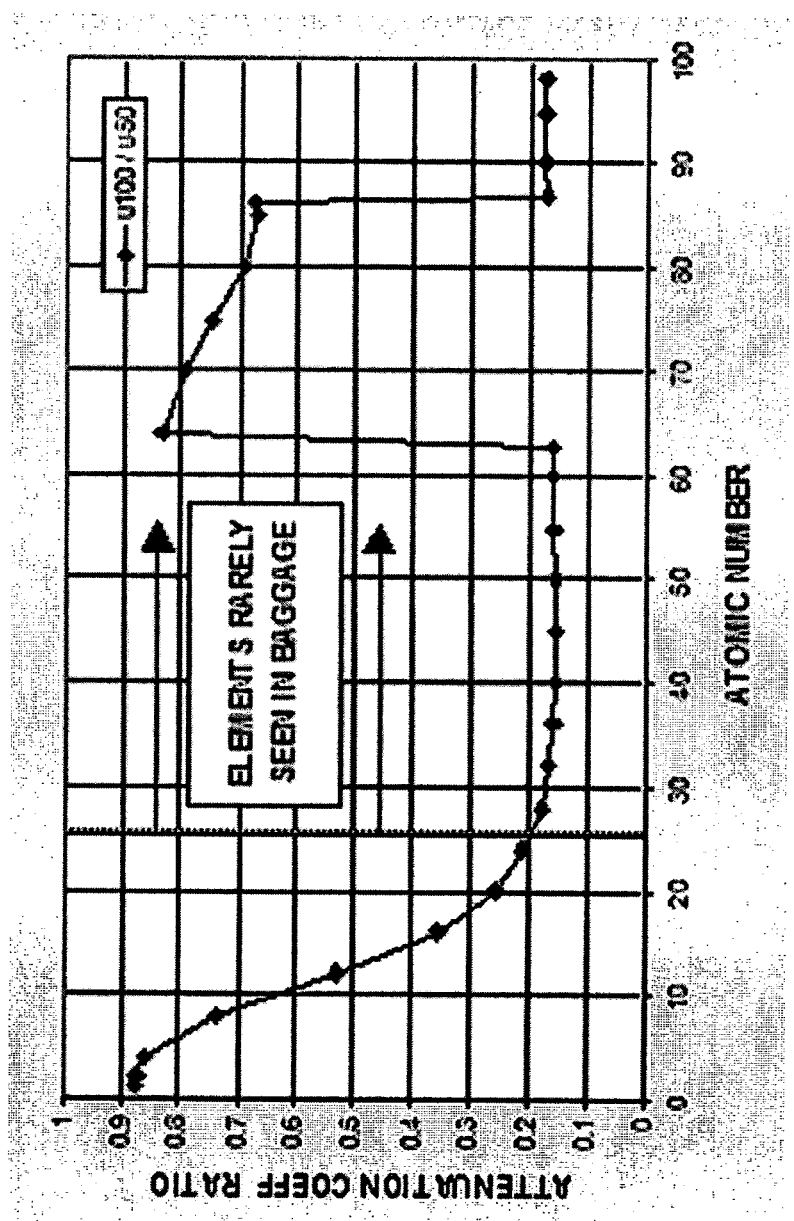
FIG. 3 is a graph illustrating acquisition of effective atomic number from dual energy attenuation measurements.

FIG. 3 illustrates information that can be obtained by measuring radiation levels at two different energies. That figure shows the ratio of the attenuation coefficient at 100 keV to that at 50 keV as a function of atomic number. The ratio decreases smoothly as a function of atomic number (Z), apart from anomalous behavior in the high Z region induced by k-edges. The ratio of attenuation of radiation at a low versus high energy provides an indication of the atomic number of the material through which the radiation passed. In particular, the HI to LO attenuation ratio can be used to determine Z with good sensitivity below approximately Z of 26 (iron).

Figure 4:
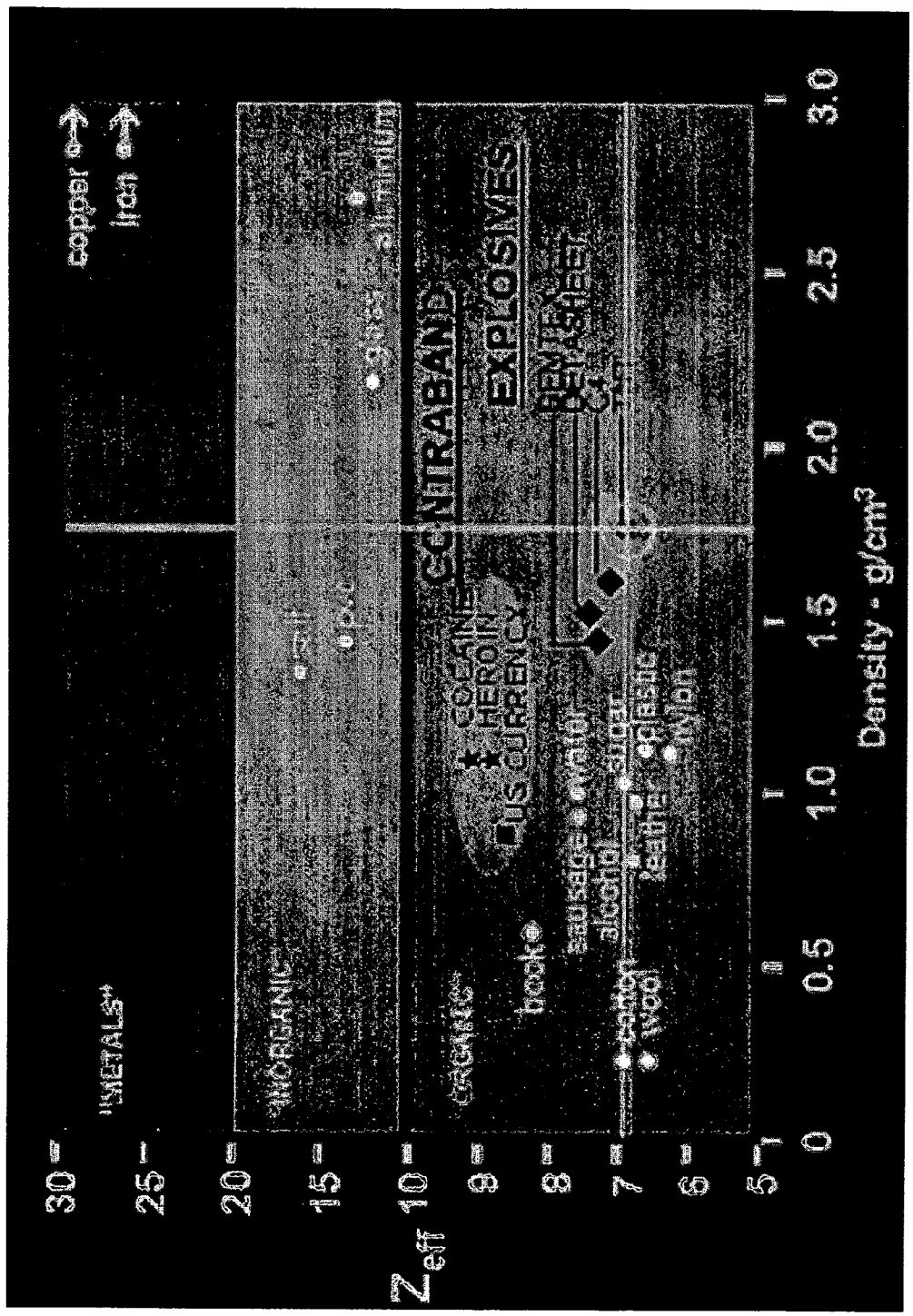
FIG. 4 is a graph illustrating fusion of data from a dual energy single view image and a computed tomographic image.

The benefits of using information relating to effective atomic number of regions within an item under inspection is illustrated in connection with FIG. 4. FIG. 4 represents a plot of effective atomic number versus density of many types of objects that may be in luggage as well as many explosives and other contraband objects.

Various types of objects fall into bands of effective atomic number, which are pictured in FIG. 4 as being metal, inorganic or organic. Contraband items, such as explosives or drugs, fall in the band generally identified as "organic." Information needed to assign items to bands based on effective atomic number can be obtained from the dual energy single view sub-system.

Objects represented within the organic band may be segregated by density to more precisely identify those objects. Information needed to attach a density to objects may be obtained from an image created with cone beam CT imaging sub-system 100. For example, explosives tend to fall into a density range that is relatively high for organic material and low for metals and ceramics. In FIG. 4, the crosshairs show how the system can target a particular explosive, such as TNT, by looking for portions of images of the item under inspection that have a specific effective atomic number and density.

Cone beam CT imaging sub-system 100 may generate data that creates a three-dimensional representation of the item under inspection. Segmentation of materials within the baggage or other item under inspection to identify objects within that item is made relatively straightforward. With sufficient CT resolution, even thin objects, such as sheet explosives can be well delineated.

In this way, information about objects obtained from multiple imaging sub-systems may be fused for an accurate detection of contraband items. The information need not be limited to only density and effective atomic number. A variety of other information about the so-defined objects, including mass, texture and local environment, may also play a role in the in algorithms developed for detection.

Other methods of using information from multiple imaging sub-systems are possible. One approach to combining data from a single view and CT system is described in pending U.S. patent application Ser. No. 10/068,459 to Bijjani, et al., titled "METHOD AND APPARATUS FOR TRANSMITTING INFORMATION ABOUT A TARGET OBJECT BETWEEN A PRESCANNER AND A CT SCANNER," filed Feb. 6, 2002, and published as 2003/0147489 A1, now U.S. Pat. No. 6,816,571, which is hereby incorporated by reference. In that application, the density information is used to identify regions of the item under inspection that represent objects. Regions representing objects are also identified based on the projection image, which, because the projection image is a dual energy image, allows assigning effective atomic number information to the objects. The segmentation of the item under inspection into regions representing objects based on the projection image can be improved based on the information from the three-dimensional image from CT sub-system 100, allowing a more accurate determination of the effective atomic number of each object in the item under inspection.

Using computer processing based on data from the CT sub-system 100 to improve the representation of objects and/or to improve the accuracy with which objects identified from the projection image are identified as contraband can have a further advantage. The projection image can be formed with a relatively high resolution without requiring large amounts of data to be collected or processed. Thus, the projection image may be displayed for the operator with objects in the item under inspection more accurately depicted or identified as contraband based on the fusion of information from multiple imaging sub-systems.

The cone beam CT imaging sub-system 100 simplifies the fusion of single view and CT information in comparison to prior art systems, because the single view imaging sub-system 210 will not have the pre-screening task of deciding where to perform slices since full 3-D CT is being performed. The single view and CT imaging sub-systems can significantly aid each other in the process of segmentation because image data can be corresponded on a line-by-line basis. The high resolution single view sub-system will be useful in picking up certain information that the CT may miss, for example, vertically oriental sheet explosives.

Figure 5:
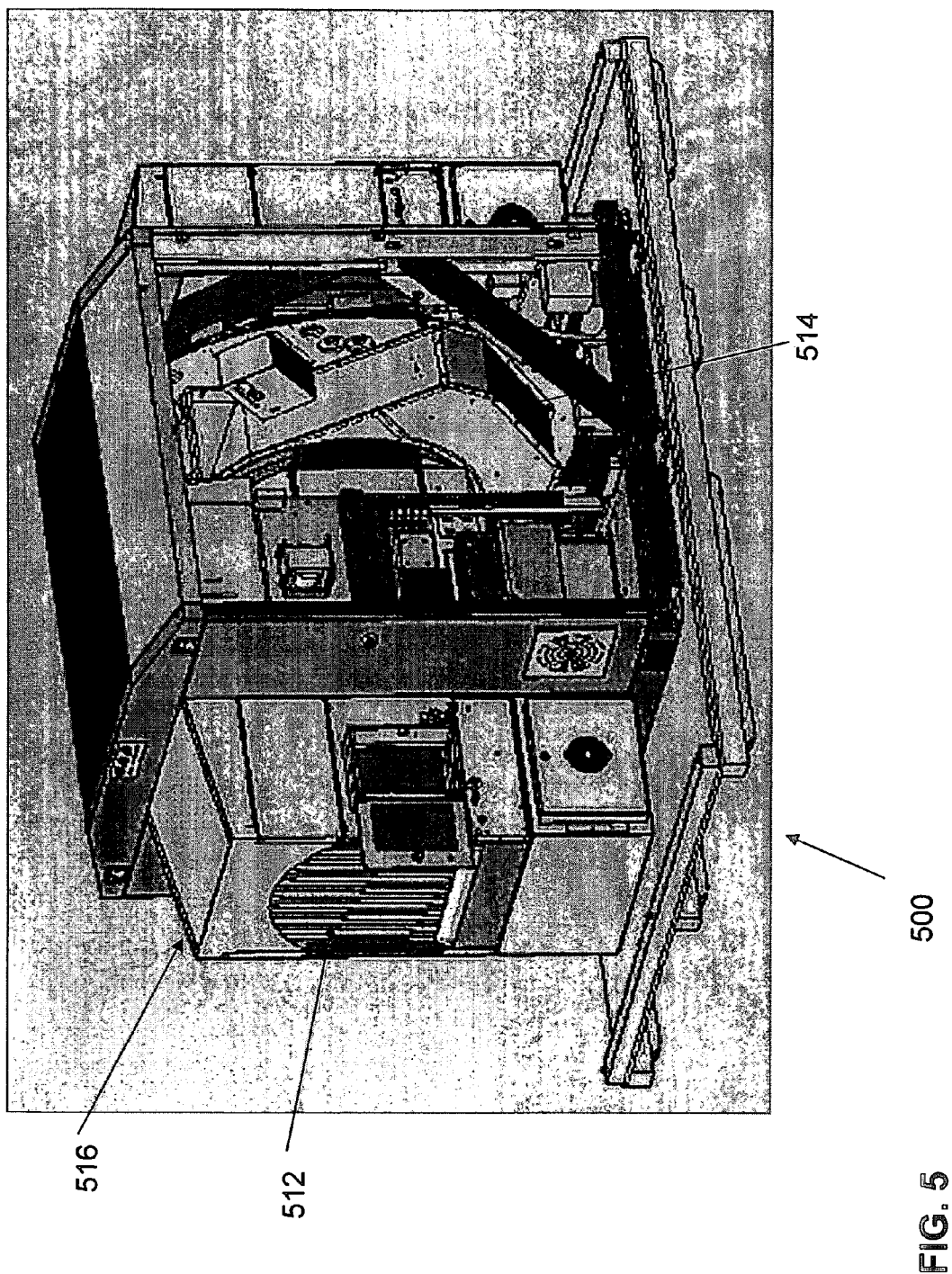
FIG. 5 is a sketch of an inspection system for acquiring dual energy image information and a computed tomographic information.

FIG. 2 shows, in somewhat schematic form, the interconnection of major components in a contraband detection system having a single view imaging sub-system 210 and cone beam CT imaging sub-system 100. FIG. 5 shows an embodiment of such an contraband detection as it may be constructed.

Contraband detection system 500 has an architecture similar to an existing product, known as the VCT-30 sold by L-3 Communications and Detections Systems, Inc. The single view sub-system and large-angle cone beam CT sub-systems are housed in the same frame and share a common conveyor, which has a motion controller for precise registration of the single view and CT images. Overall length is relatively compact, but tunnel aperture may be 100 cm or more. Such a tunnel may accommodate baggage or other items under inspection up to 100 cm wide and 50 cm high. In this embodiment, bags with heights up to 80 cm can also be inspected, if relatively narrow.

FIG. 5 shows a tunnel opening 512. One section of system 500 includes a gantry 514 that houses both the source and detector array used for the cone beam CT imaging sub-system 100. A motor (not shown) drives gantry 514 to rotate the source and detector array around an inspection area.

A single view sub-system is installed at 516. Items under inspection placed in the tunnel are moved on a conveyor through the system past the single view and the CT sub-systems.

System 500 may include or be connected to one or more computers that can be programmed to perform algorithms that automatically find threat objects within baggage with low false alarm rates in real time. For example, the methods described in the pending patent application to Mahdavieh, filed as U.S. patent application Ser. No. 10/896,753 "METHOD AND APPARATUS FOR DETECTING SHEET EXPLOSIVES," filed Jul. 22, 2004, and U.S. Published Application 2005/0036689, titled "METHODS AND APPARATUS FOR DETECTING OBJECTS IN BAGGAGE" which claims priority thereto, and are both hereby incorporated by reference. The fusion of CT and dual-energy single view technologies makes for a more robust system, capable of adapting to a variety of threats and countermeasures that will inevitably emerge in the years to come. However, advantages of the large-angle cone beam CT system can be realized without the use of single view sub-system. Alternatively, the large-angle cone beam CT may be employed in conjunction with other styles of pre- or post-scanners.

The arrangement of FIG. 5 is illustrative, but is not required. For example, the single view scanner may be physically separate from the CT scanner. The units need not be physically present in the same location. For example, the single view scanner may be used for level 1 scanning with baggage information acquired by the single view scanner being passed on for high level inspection only when suspicious objects are identified in an item under inspection or when the item under inspection can not be "cleared" (i.e. inspection by the single view system is not adequate to allow a conclusion to be made that the item is free of all objects that could be threats).

The contraband detection system as described above offers the possibility of full 3-D CT reconstruction in combination with full dual-energy single view imaging. It is described in connection with baggage inspection for detection of explosives. Such a system may be used to inspect checked luggage or carry on luggage at airports, train stations or other transportation facilities. Such a system may also be used to inspect containers or other packages or cargo before shipping. Further, such a system may be used to screen items for other types of contraband, such as drugs or weapons. Such a contraband detection system may find use in wide variety of applications, for example, non-destructive testing, sortation, grading, recognition of defects or inclusions, material identification or medical diagnosis or treatment. It should be appreciated that the single view projection x-ray system may be a pre-screener as is sometimes used in connection with a CT system to select locations in the item under inspection at which to acquire "slices" for further inspection. However, to combine single view and CT image information, it is not necessary that the single view projection information be acquired first. Other pre-screeners or post-screeners might be used instead of or in addition to the single view system.

Such a contraband detection system offers a straightforward approach for dramatically improving baggage screening operations. In comparison to a prior art inspection system, a cone beam CT imaging sub-system 100 may be operated to provide roughly 2.5 increase in throughput that far outweighs any increase in system cost, and will result in a significantly reduced cost per bag inspected. The expected reduction in false alarms by 30 to 50% translates into a labor savings in the number of bags that require operator inspection. If operator inspection is required, the high resolution single view image will facilitate the speed and accuracy of threat decision-making.

However, an inspection system having a cone beam CT imaging sub-system 100, either alone or in combination with a single view imaging sub-system, need not change the current screening environment except through increased efficiency in labor use. The entire system can occupy roughly the same floor-space and locations as existing certified x-ray screening equipment. Operator stations and human factors can remain largely the same.

Having thus described several aspects of at least one embodiment of this invention, it is to be appreciated various alterations, modifications, and improvements will readily occur to those skilled in the art.

For example, one of skill in the art will appreciate that a beam does not have an abrupt end as pictured. Rather, the beam width is usually defined by locations at which the magnitude of the beam drops below a certain fraction of its peak value. Also, because there is no abrupt end to the beam, it may desirable for radiation in the beam to extend beyond the edges of the array to ensure that detectors near the edge of the array receive adequate levels of radiation.

Such alterations, modifications, and improvements are intended to be part of this disclosure, and are intended to be within the spirit and scope of the invention. Accordingly, the foregoing description and drawings are by way of example only.

What is claimed is:

1. A method of analyzing an item for the presence of contraband, comprising:
   a) forming a projection image of the item with a first resolution using a multi-energy scanner;
   b) forming a computed tomography image of the item with a second resolution, less than the first resolution, using a cone beam computed tomography scanner; and
   c) forming, based at least on the projection image and the computed tomography image, an image representative of an object within the item, including an indication of an effective atomic number of the object.

2. The method of claim 1 wherein forming a computed tomography image comprises forming an image with a resolution of about 2 mm.

3. The method of claim 1, wherein forming an image representative of an object within the item, comprises delineating the object using density information obtained from the computed tomography image and obtaining effective atomic number from the projection image, corrected based on the delineation of objects.

4. The method of claim 1, wherein forming a computed tomography image comprises forming an image with a detector array spanning approximately 120 degrees of arc.

5. The method of claim 1, wherein the method additionally comprises moving the item along a conveyor having a direction of motion and forming a computed tomography image comprises forming an image with a detector array having a width in the direction of motion of at least 25 cm.

6. The method of claim 5, wherein forming a computed tomography image of the item comprises reconstructing a representation of the item from a helical scan of the item.

* * * * *